United States Patent [19]

Buchwald et al.

[11] Patent Number: 4,610,658
[45] Date of Patent: Sep. 9, 1986

[54] AUTOMATED PERITONEOVENOUS SHUNT

[76] Inventors: Henry Buchwald, c/o University of Minnesota Medical School, Minneapolis, Minn. 55455; Eugenio Guzman, 2710 N. Dale, #204, Roseville, Minn. 55113; Bruce D. Wigness, University of Minnesota, 2630 University Ave. S.E., Minneapolis, Minn. 55455

[21] Appl. No.: 703,758

[22] Filed: Feb. 21, 1985

[51] Int. Cl.⁴ ............................................. A61M 5/00
[52] U.S. Cl. ...................................... 604/9; 604/152; 417/417
[58] Field of Search ....................... 604/8–10, 604/247, 185, 323, 151, 152, 891; 417/417

[56] References Cited

U.S. PATENT DOCUMENTS

| | | |
|---|---|---|
| 3,233,610 | 2/1966 | Wade ............................................. 604/9 |
| 3,608,088 | 9/1971 | Dorman et al. . |
| 3,683,929 | 8/1972 | Holter ............................................ 604/9 |
| 3,910,283 | 10/1975 | Leveen . |
| 4,240,434 | 12/1980 | Newkirk . |
| 4,457,752 | 7/1984 | Vadasz ...................... 604/891 X |
| 4,487,556 | 12/1984 | Wiernicki ..................... 417/417 |
| 4,487,603 | 12/1984 | Harris ......................... 604/891 X |

Primary Examiner—Stephen C. Pellegrino
Attorney, Agent, or Firm—Burd, Bartz & Gutenkauf

[57] ABSTRACT

An implantable, anti-reflux, fluid displacement peritoneovenous shunt system. The system includes a double chambered multi-micro-orifice ascites collection device, a magnetically driven pump, and an anti-reflux, anti-backdiffusion, non-thrombogenic catheter tip, all connected by flexible tubing. The shunt is used to transfer fluid from the peritoneum to the cardiovascular system to prevent accumulation of fluid within the peritoneal cavity. The magnetically operated pump may be of either the reciprocating diaphragm or piston type or it may be a rotary driven bellows displacement pump.

10 Claims, 15 Drawing Figures

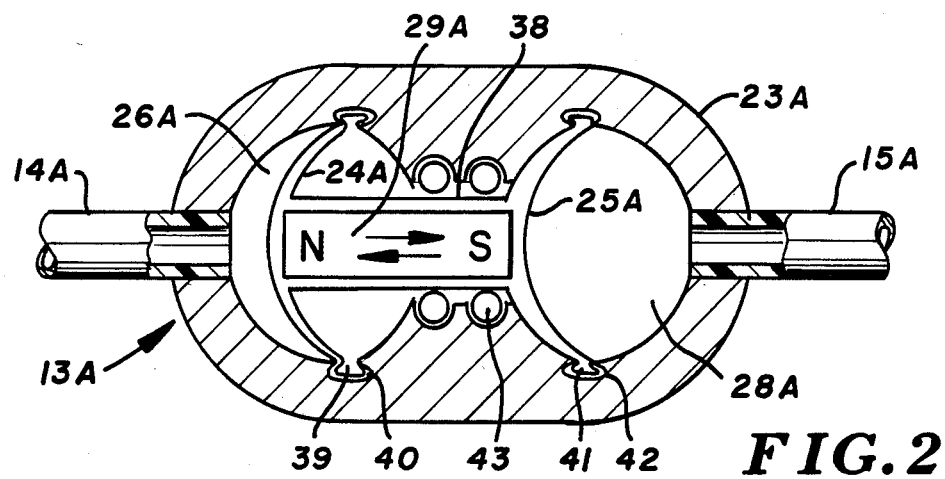
FIG.2
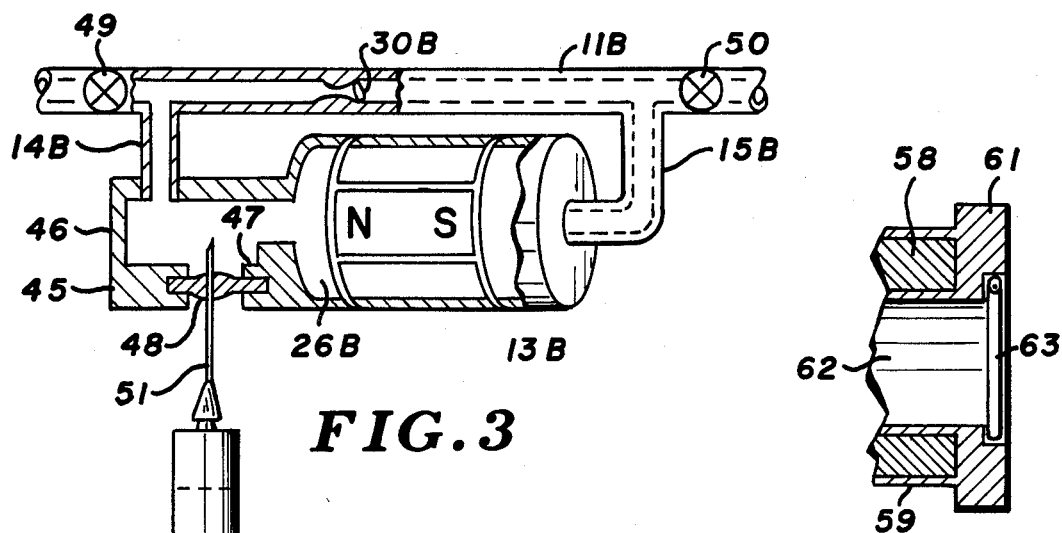
FIG.3
FIG.6
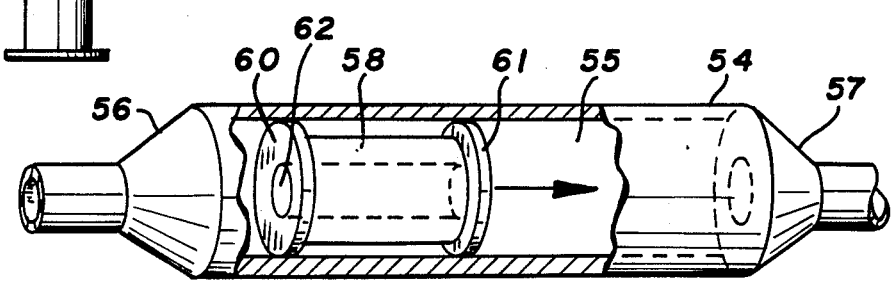
FIG.4
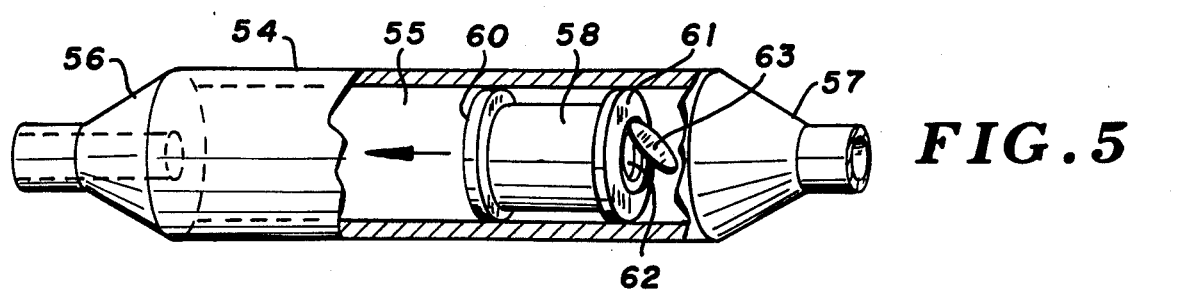
FIG.5

AUTOMATED PERITONEOVENOUS SHUNT

FIELD OF THE INVENTION

BACKGROUND OF THE INVENTION

This invention relates to an implantable anti-reflux fluid displacement peritoneovenous shunt used to transfer an unwanted accumulation of body fluids from a body cavity to a site where they can be processed by the body. The primary use for the shunt is in the treatment of patients with ascites by the displacement of accumulated peritoneal cavity fluid into the systemic venous circulation.

This application is related to our copending U.S. application Ser. No. 598,243, filed Apr. 4, 1984, entitled Compression Pump-Catheter and directed to a manually operable ascites shunt. The disclosure of that application is incorporated herein by reference. The device of the aforesaid application is a peritoneovenous shunt in which ascites fluid is transferred from the peritoneum to the vasculature via a manually operated compression pump. That device is not an alternative for certain patients who require peritoneovenous shunting but for a variety of reasons are unable to perform the pumping mechanics. The present invention is directed to a peritoneovenous shunt which features automation of the earlier design, thus expanding the benefit of this therapy to a broader population of patients and providing greater convenience to existing patients.

As described in application Ser. No. 598,243, there is evidence that ascites occurs with the obstruction, or increase in pressure, of hepatic lymphatics with a subsequent oozing of lymphatic fluid from the surface of the liver. If the fluid flux is high, especially in an individual with liver disease and portal venous system hypertension, there is inadequate re-absorption of this fluid and it accumulates within the peritoneal cavity.

In addition to the discomfort and pressure problems associated with massive abdominal distention due to ascites, patients with ascites are more prone to develop reflux esophagitis, respiratory failure, abdominal wall hernia defects, renal failure, and an increased susceptibility to infections.

Besides its use in the management of ascites, the shunt of this invention can, with modest modifications, be utilized for the transfer of other body fluids, e.g., the displacment of brain ventricular fluid in hydrocephalus to either the right atrium of the heart or to the peritoneal cavity.

THE PRIOR ART

As described in the aforesaid copending application, the most pertinent known prior art is Le Veen U.S. Pat. No. 3,910,283 which discloses an apparatus for the continuous drainage of ascitic fluid from the peritoneum through a one-way valve into a silicone rubber tube which terminates in a jugular vein or other large vein for passage of the fluid into the vascular system, and Newkirk U.S. Pat. No. 4,240,434 which discloses a similar device called the Denver shunt. To date these two devices are the most used shunting devices for treating patients with ascites. Their use remains limited due to a high incidence of complications, primarily disseminated intravascular coagulopathy (DIC).

SUMMARY OF THE INVENTION

Broadly stated, the implantable anti-reflux fluid displacement peritoneovenous shunt according to this invention consists of three parts, connected by flexible tubing: (1) a double chambered multi-micro-orifice collecting device; (2) an anti-reflux, anti-backdiffusion magnetically driven fluid pump having at least one variable volume chamber; and (3) an anti-reflux, anti-backdiffusion, non-thrombogenic catheter for intravascular placement. The fluid pump may be of either the reciprocating diaphragm or piston variety. It includes an internal magnetic armature which is free to move within a housing and which is transcutaneously magnetically coupled to an external driver during fluid transfer. The movement of the internal magnet is defined by the corresponding movement of the external driver magnet to which it is coupled. With the proper valving, the movement of this armature results in the active transfer of fluid away from the site of unwanted accumulation. Alternatively, the fluid pump may be rotary driven from an external rotary source magnetically coupled to a bellows displacement pump operated by an internal coupled magnetic screw jack.

BRIEF DESCRIPTION OF THE DRAWINGS

The invention is illustrated in the accompanying drawings in which corresponding parts are identified by the same numerals and in which:

FIG. 2 is an elevation in section of a slightly modified form of diaphragm pump;

FIG. 3 is an elevation, partly broken away and in section, showing a further modified form of diaphragm pump;

FIG. 4 is an elevation, partly broken away and in section, showing a form of spool piston pump in pumping mode;

FIG. 5 is a similar elevation, partly broken away and in section, of a spool piston pump in its return mode;

FIG. 6 is a fragmentary vertical section showing a form of spool piston flap valve;

DETAILED DESCRIPTION OF THE PREFERRED EMBODIMENT

Figure 1:
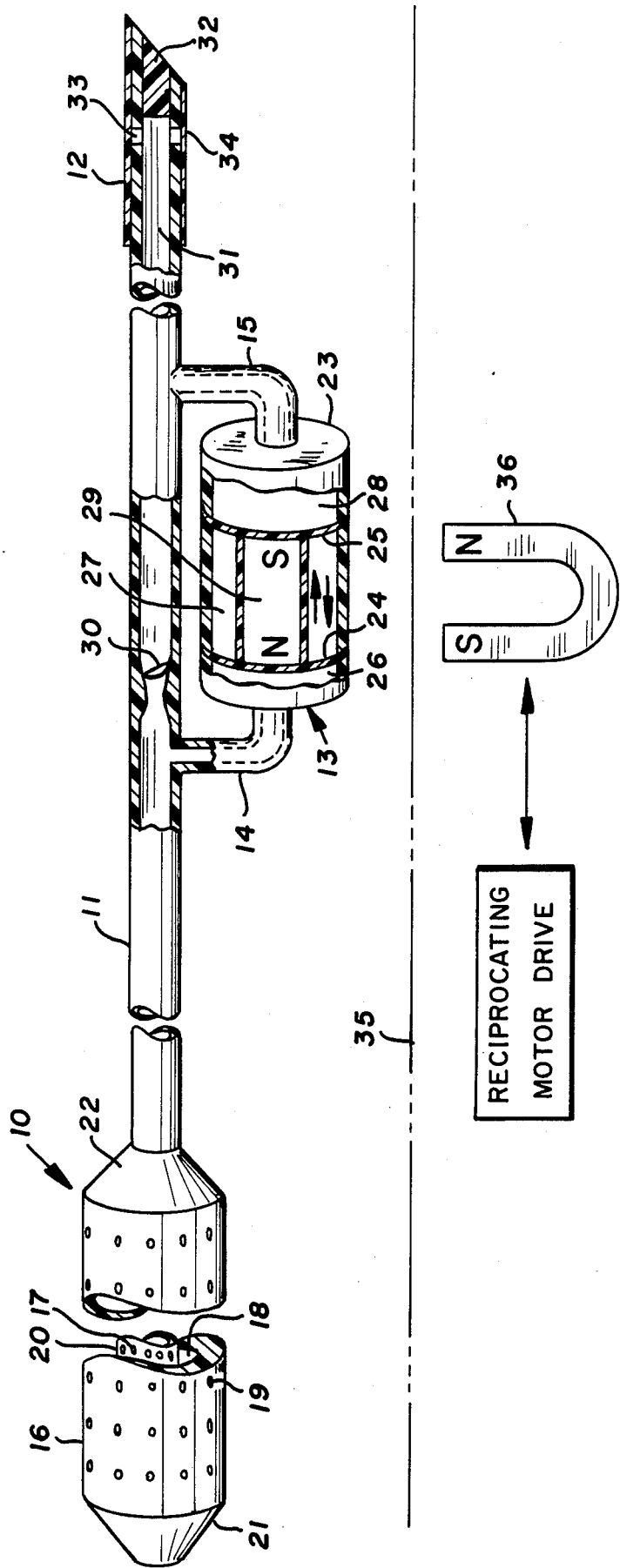
FIG. 1 is an elevational view of one form of peritoneovenous shunt according to the present invention, with portions shown partly broken away and in section to reveal structural details.

Referring now to FIG. 1, the peritoneovenous shunt according to the present invention includes a sieve-like elongated collecting device 10 connected by a catheter or similar length of flexible tubing 11 to a check valve catheter tip 12. A diaphragm pump 13 is connected in parallel with catheter 11 by means of tubes 14 and 15.

As described in the aforesaid copending application, the ascites collector 10 is constructed from an elongated outer section of flexible tubing 16 and an inner section of flexible tubing 17 of substantially the same length. The tubing sections 16 and 17 are concentrically disposed with an annulus 18 between. Tubing section 16 is provided with a myriad of small diameter perforations 19 to give the tubing section a sieve-like structure. Similarly, the inner tubing section 17 is provided with a myriad of small diameter perforations 20.

The distal or upstream end of outer tubing section 16 is preferably closed by a plug closure 21. Similarly, the distal end of the inner tubing section 17 is also closed by a plug. Both distal ends of the tubing sections may be closed by a single plug means which also then functions to maintain the concentric arrangement of the tubing sections. The distal end of tubing section 11 is inserted into the proximal or downstream end of inner perforated tubing section 17. A plug 22 serves to close the annulus 18 at the proximal end of the collection device and to connect the collector to tubing 11.

The diaphragm pump 13 comprises a housing 23 having a cylindrical chamber divided into three parts by flexible diaphragms 24 and 25. The peripheries of diaphragms 24 and 25 are sealed to the inside housing wall in fluid-tight relationship. The housing may be formed, for example, from three segments of tubing adhesively secured together with the peripheries of the diaphragms sandwiched between adjacent segments. The first housing chamber 26 is between the distal end wall of the pump housing and diaphragm 24. The intermediate chamber 27 is between the diaphragms. Chamber 28 is between diaphragm 25 and the proximate end wall of the pump housing. A magnetic armature 29 in the form of a short bar magnet is located in chamber 27 between of and connected to diaphragms 24 and 25, and supported by them. A unidirectional flap valve 30 is located in tube 11 between the tubes 14 and 15 connecting pump 13 to tube 11.

The catheter check valve tip 12 at the end of tubing 11 is of the type disclosed in Dorman application Ser. No. 245,379, the disclosure of which is incorporated herein by reference. The proximal end of bore 31 is closed by means of plug 32. One or more cross bore ports 33 extend through the tubing wall immediately upstream from the plug. Ports 33 are covered by means of a thin elastic sleeve 34 which is adhesively attached to the tubing upstream from the cross bore ports. The end of the catheter tip 12 and the end of sleeve 34 preferably terminate in a plane at an acute angle to the longitudinal axis of the catheter to facilitate entry into a blood vessel.

The peritoneovenous shunt is implanted using standard surgical techniques with the collector 10 being located in the peritoneum, the diaphragm pump 13 being positioned in a comfortable and convenient subcutaneous location closely adjacent to the skin 35 of the patient, and the proximal check valve tip 12 being threaded into the desired blood vessel. The diaphragm pump 13 is operated by means of an external magnetic driver 36 held against the surface of the skin 35 in close proximity to the implanted pump housing. The poles of the magnetic driver 36 are opposite to the poles of magnetic armature 29. As the drive is reciprocated, the armature is reciprocated and drives the diaphragms 24 and 25. The system is frictionless since the magnetic armature is held suspended by the diaphragms. The external magnetic driver may range in complexity from being simply a hand-held magnet to motorized controlled drives, as described in greater detail hereinafter.

In operation, when the armature 29 is moved in the proximate direction, the diaphragms 24 and 25 are flexed. As diaphragm 25 is driven toward chamber 28, the pressure within that chamber increases until it exceeds the combined forces of the elastic squeeze of the sleeve 34 of the check valve catheter tip 12 plus the blood pressure at the tip of the catheter. At that point, as the volume of the chamber becomes smaller, fluid from within the pumping chamber 28 is transferred to the vasculature. Fluid transfer continues until the end of that stroke of the diaphragm is reached. At the same time, flexing of diaphragm 24 draws fluid from the collector 10 through tube 14 into chamber 26 whose volume is becoming correspondingly larger, allowing the armature to stroke without drawing a partial vacuum on the back side. When the pump stroke is reversed, the catheter check valve 12 closes, a pressure drop occurs in chamber 28, and fluid is forced from chamber 26 and is aspirated into chamber 28 through flapper check valve 30. The pumping cycle is repeated as often as necessary to withdraw the accumulated ascites fluid by reciprocating the external magnetic drive. Repetition of this two stroke cycle is carried out for a time period that is either prescribed by a physician or determined by reaching an endpoint that is measured by sensors on the external driver or a patient perceived sensory endpoint.

Referring to FIG. 2, there is shown a modified form of diaphragm pump 13A. This form of pump has a cylindrical ovoid body 23A having two generally spherical chambers 26A and 28A separated by a constricted passage 38. A flexible diaphragm 24A is located in chamber 26A. Diaphragm 24A has a flanged periphery 39 which is received in a groove 40 in the outer periphery of chamber 26A to maintain a fluid-tight seal. Similarly, flexible diaphragm 25A located in chamber 28A has a flanged periphery 41 engaging groove 42 in the outer periphery of the chamber and similarly sealed. Diaphragms 24A and 25A are interconnected by magnetic armature 29A. The armature rides on bearings 43 located in the constricted throat 38 between the chambers. The space between the diaphragms may optionally be filled with a lubricating fluid. This form of pump is connected in parallel in a collector-catheter-check valve tip system, as already described, by means of connecting tubing 14A and 15A. The system is implanted and the pump is driven from an external magnetic source in the manner already described.

It is sometimes desirable that the physician be allowed to percutaneously enter a plenum with a hypodermic needle for the purpose of injecting diagnostic or shunt maintenance fluid or for withdrawing a sample of the body fluid being transferred. A means for accomplishing this is shown in FIG. 3. Pump 13B is identical in all material respects to pumps 13 and 13A already described, except that a plenum housing 45 enclosing chamber 46 is located between pump chamber 26B and connecting tubing 14B. Entry to the plenum chamber 46 is through a septum passage 47 having a self-sealing closure 48 capable of multiple punctures without leaking. Closure 48 may be formed from silicone rubber, for example. A pair of transcutaneously actuated valves 49 and 50, as described in detail hereinafter, are interposed in catheter 11B. The distal valve 49 is located upstream from the entry point of connecting tubing 14B. The proximate valve 50 is located downstream from the entry point of connecting tubing 15B. This permits either intravascular or intraperitoneal infusion, or withdrawal of peritoneal fluid by means of hypodermic needle 51 and syringe 52. For example, if the performance of a shunt begins to degrade, the physician may first inject radio-opaque dye through the intravascular end of the shunt by closing valve 49 and viewing the passage of the dye fluoroscopically. Then, by closing valve 50 and opening valve 49, radio-opaque dye may be injected for flow toward the collector and passage of the dye viewed fluoroscopically for obstruction. If fluoroscopic examination reveals an obstruction, the physician can close off flow to the unobstructed end, inject a fibrin degrading drug, such as streptokinase, into the obstructed end. Thereby the need for possibly subjecting the patient to shunt replacement surgery may be avoided.

Referring now to FIGS. 4 through 6, there is shown a magnetically driven piston pump. This form of pump comprises a housing 54 having an inner cylindrical chamber 55. The housing has fittings 56 and 57 at opposite ends for connecting the pump in series with catheter 11 (FIG. 1) between the ascites collector 10 and check valve tip 12. A spool piston is located for reciprocal movement within chamber 55. The spool is composed of a hollow cylindrical magnet 58 encased in a layer 59 of tetrafluoroethylene (Teflon) or similar biocompatible synthetic resinous material. A pair of spaced apart annular flanges 60 and 61 are fitted to opposite ends of magnet 58. The peripheries of the flanges engage the wall of chamber 55 in sliding sealing engagement.

A central longitudinal channel 62 is provided through the spool assembly for passage of fluid therethrough. Flange 61 is fitted with a pivoted disc flap valve 63 which seats in an annular recess in the inner periphery of the outer face of flange 61. FIG. 4 shows the piston in pumping mode with flap 63 closed. Beginning with the piston at the peritoneal end of the housing, the pressures on either side of the flap valve are equal and exceeded by blood pressure at the catheter tip. As the piston is initially driven toward the vascular end of the housing, the flap valve is forced against the face of the piston forming a tight seal which is maintained as long as the pressure of the proximal side of the flap valve is greater than the pressure of the peritoneal side. As the piston is driven further, the pressure inside the housing increases until it exceeds the combined forces of the elastic squeeze of the catheter tip check valve 12 plus blood pressure at the catheter tip. When enough pressure is built up, the elastic sleeve 34 is expanded open and fluid is forced into the vasculature. This continues until the end of the stroke, at which time the check valve at the catheter tip closes and the pressures on either side of the flap valve equilibrate. The direction of the external driver magnet reverses and, as shown in FIG. 5, the piston is driven toward the peritoneal end of the chamber. As soon as the pressure on the vascular side of the flap valve drops below that of the peritoneal side plus the structural forces within the flap valve, the flap valve bends away from the valve seat and fluid from the peritoneal space is aspirated into the vascular side of the flap valve. The fill stroke of the piston continues until the piston is stopped at the peritoneal end of the chamber and the pressures on either side of the flap valve equilibrate. As in the diaphragm design, repetition of this two stroke cycle is carried out for a time period that is either prescribed by a physician or determined by reaching an endpoint that is measured by sensors on the external drive, or a patient perceived sensory endpoint.

This form of pump is implanted under the skin in the manner already described and functions in response to a magnetic field applied by an external magnet. It has the advantage of compactness as compared to the diaphragm pump. The interconnect tubing 14 and 15 may be eliminated. This simplifies the overall design, an important consideration in implantable devices. On the other hand, proper operation of the piston assembly necessarily involves sliding surfaces requiring close tolerances between the outside diameter of the piston flanges and the inside diameter of the housing chamber. This creates the possible danger of jamming with body proteins. The piston pump may be provided with a plenum for percutaneous injection or withdrawal of fluid as described in connection with FIG. 3.

Figure 7:
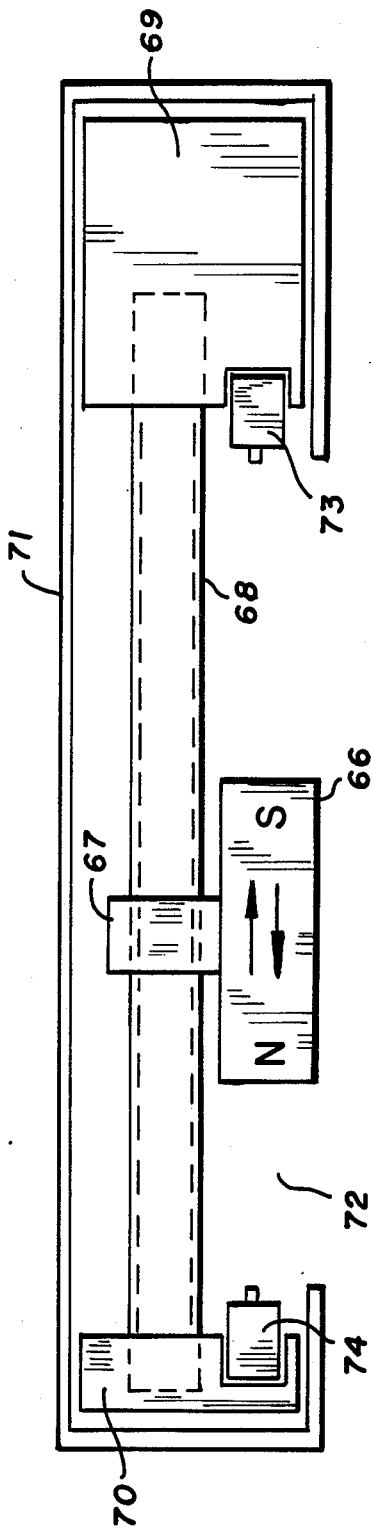
FIG. 7 is an elevation partly in section showing a form of low speed drive for a magnetic actuator.

FIG. 7 shows one form of automatic external magnetic driver for reciprocating diaphragm and piston pumps. In this exemplary form of driver mechanism, a driver magnet 66 is mounted on an internally threaded collar 67 which in turn engages a rotatable threaded shaft 68. One end of shaft 68 is coupled to a driver mechanism, such as electric motor 69, for rotation therewith. The opposite end of shaft 68 is journaled in a bracket 70 at the opposite end of a housing 71 which encloses the driver system. The housing has an opening 72 adjacent to the path of the driver magnet in its reciprocation along shaft 68. The driving housing is strapped or otherwise held against the skin of the patient with opening 72 adjacent to the implanted magnetically operated diaphragm or piston pump. Motor 69 is driven by any suitable power source, preferably a rechargeable battery pack. Limit switches 73 and 74 are disposed at opposide ends of the path of magnetic driver 66 and control the power circuit to reverse the direction of rotation of motor 69 at the end of each stroke of the driver magnet.

The driver system may embody electronic controls and sensors including any combination of speed controls, timers, random access memory (RAM) and read only memory (ROM) chips, and alarms, etc. For example, a force sensor on the linkage between the motor and the driver magnet may be set up to detect a sudden increase in force necessary to move the pump armature. This would be an indirect measure of when the peritoneum has been emptied and consequently would signal the end point for that session of therapy. The drive system could then be turned off automatically or an alarm sounded so that the patient may turn off the drive. A combination of that same force sensing strategy, along with a counter and a RAM memory chip, may be teamed up to log in the number of strokes and duration of each therapy session for periodic review by the attending physician. The driver system may be designed with a degree of sophistication scaled to the needs of the patient to be treated.

Figure 8:
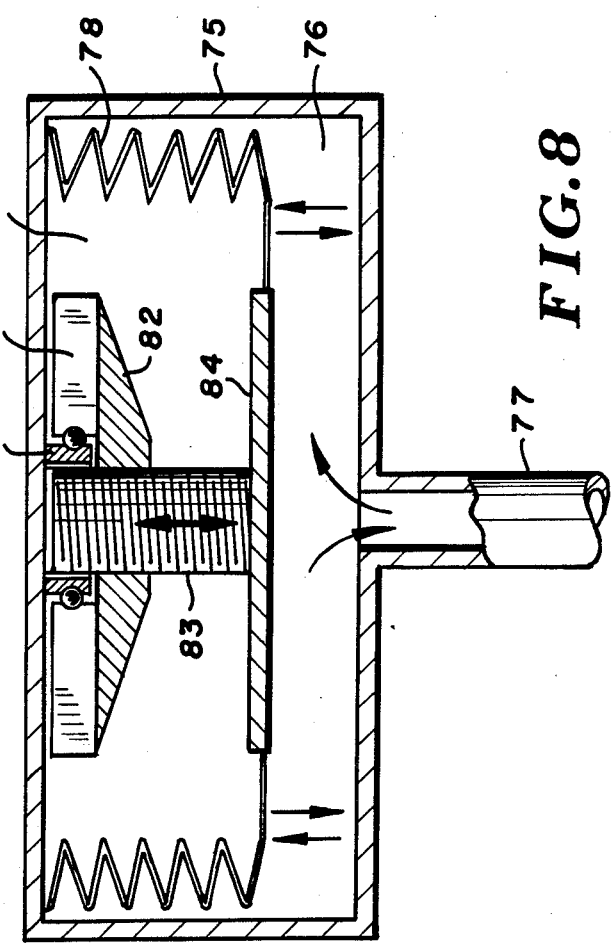
FIG. 8 is an elevation in section of a rotating armature bellows pump.

FIG. 8 is exemplary of a form of fluid pump which employs a rotating rather than a reciprocating driver magnet. This form of pump includes a cylindrical housing 75 enclosing a chamber 76 which is connected by means of tubing 77 to catheter 11 of the shunt system at a location (FIG. 1) between flap check valve 30 and catheter tip 12. A bellows 78 comprised of a stack of a plurality of concentric flat annular rings and a circular bottom wall is disposed within housing chamber 76 and defines a further chamber 79. A rotary magnet armature 80, which may be a ring magnet or a plurality of radially arrayed bar magnets, is journaled on bearing 81 for rotation within chamber 79. A nut 82 is coupled to the magnet armature for rotation therewith. A screw jack is formed as nut 82 in turn engages threaded shaft 83 which is concentrically disposed within the pump housing and is connected to disc plunger 84 which comprises part of the bottom wall of the bellows. The bellows pump is likewise implanted surgically with the magnetic armature closely underlying the skin of the patient.

When the magnet armature is rotated by exposure to an external rotating magnetic field, the armature drives nut 82 in rotation about shaft 83 causing the bellows to expand or contract dependent upon the direction of rotation. This in turn causes the volume of chamber 76 to contract or expand correspondingly to expel collected body fluid from the chamber or to draw such fluid into the chamber.

Chamber 79 preferably includes a stable volatile liquid that is in equilibrium with its vapor phase over the entire stroke of the bellows at body temperature (approximately 37° C.) to compensate for pressure changes which might otherwise result and interfere with pump performance. Suitable volatile liquids include the halogenated hydrocarbons available as Freon, ethyl ether, tetramethylcylene, methylformate, and the like.

One exemplary form of rotary magnetic drive is that disclosed in Dorman et al U.S. Pat. No. 3,608,088. The motor drive is preferably programmed so that when the magnetic rotor makes a given number of turns (e.g., 10 to 20) in one direction to achieve the aspiration stroke, a sensor is tripped which in turn electronically reverses the external drive rotor for the delivery stroke of the cycle.

Figure 9:
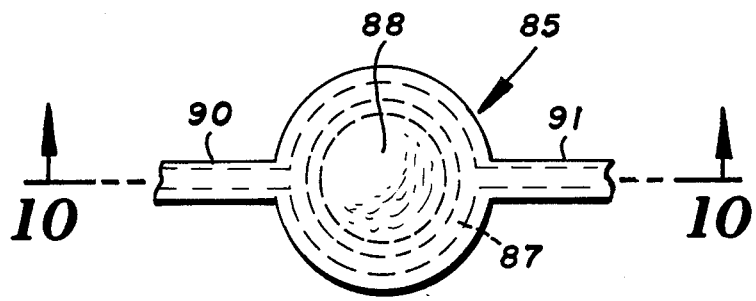
FIG. 9 is a top plan view of one form of transcutaneously actuated valve.
Figure 10:
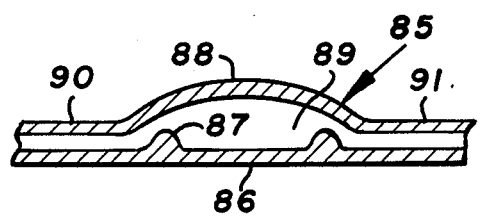
FIG. 10 is a section on the line 10—10 of FIG. 9 and in the direction of the arrows showing the valve in open position.
Figure 11:
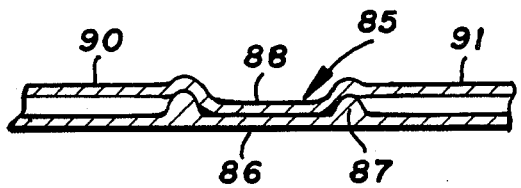
FIG. 11 is a similar section showing the valve in closed position.
Figure 13:
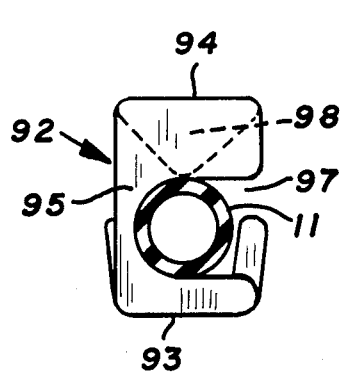
FIG. 13 is a left end elevational view thereof.
Figure 12:
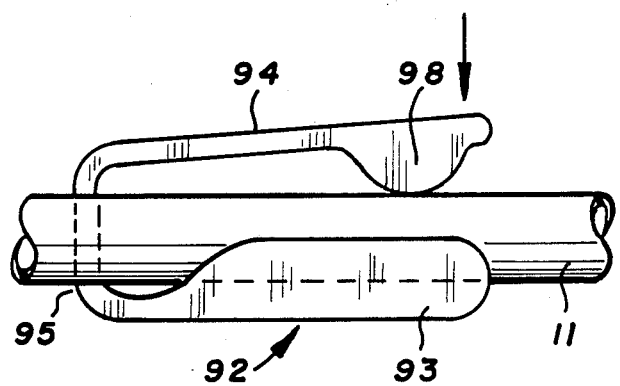
FIG. 12 is a side elevational view of another form of transcutaneously actuated valve.
Figure 14:
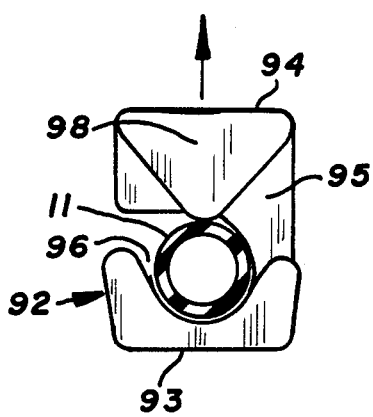
FIG. 14 is a right end elevational view thereof showing the valve in open position.
Figure 15:
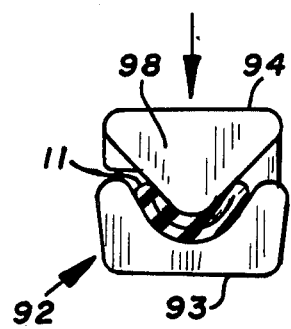
FIG. 15 is a similar end elevational view showing the valve in closed position.

Referring now to FIGS. 9 through 11, there is shown one form of transcutaneously actuated valve which may be utilized in the shunt system of FIG. 3. Valve 85 comprises a housing having a flat circular bottom wall 86 having an annular ridge 87 on its inside surface spaced slightly inwardly from its outer periphery. Valve 85 also includes a circular resilient dome-like top wall 88 overlying bottom wall 86. A chamber 89 is defined in the space between bottom and top walls 86 and 88, respectively. Tubular fittings 90 and 91 communicate with chamber 89 to permit connection of the valve to catheter 11. The shunt system is implanted with valve 85 disposed under and generally parallel to the skin surface with top wall 88 outermost. Then, as seen by comparison of FIGS. 10 and 11, slight finger pressure exerted through the skin against the dome-like top wall 88 urging it into engagement with the bottom wall 86 in the space within annular ridge 87 causes chamber 89 to collapse and flow through the valve to cease.

An alternative form of transcutaneously actuated pinch valve 92 is shown in FIGS. 12 through 15. Pinch valve 92 comprises a slightly resilient C-shaped device having a bottom member 93, a top member 94, and interconnecting end member 95. The outermost end of bottom member 93 is formed with an inwardly facing U-shaped channel 96 adapted to receive and engage catheter 11. End wall 95 has an opening 97, preferably open on one side for easy engagement with catheter 11, to receive catheter 11 with a snug fit so that the pinch valve remains in place on the catheter. The outer end of top member 94 has a generally conical bulbous protrusion 98 on its inner surface overlying channel 96. A shunt system utilizing pinch valve 92 is implanted with top valve member 94 underlying and parallel to the skin surface. As seen by comparison of FIGS. 14 and 15, finger pressure exerted against member 94 causes protrusion 98, in cooperation with channel 96, to collapse catheter 11 and close off liquid flow through the catheter. Pinch valve 92 may be formed from any of a variety of biocompatible materials, such as molded synthetic resinous plastic or stainless steel, for example. Although the top and bottom members are generally rigid, sufficient resiliency is afforded through the connecting end wall 95 to permit squeezing of the top and bottom members sufficiently to pinch off liquid flow through the catheter.

All of the implantable structure which is in contact with body fluids or tissue is composed of inert stable non-toxic biocompatible materials. A preferred material for the tubing components is medical grade silicone rubber tubing and a preferred material for the several plugs and connections is medical grade Sileastic adhesive. A preferred material for check valve sleeve 34 is silicone rubber with the sleeve separated from the rest of the catheter by a film of low surface energy material, such as polytetrafluoroethylene (Teflon). The magnetic armatures are desirably formed from a high energy magnetic iron-aluminum-nickel-cobalt-copper alloy material, such as that sold under the trade names Alnico VIII or Alnico IX, or equivalent material.

In some instances where economy of size is a critical factor, magnetic samarium-cobalt, or other high energy rare earth magnetic alloys may be used. All magnets are preferably coated with polytetrafluoroethylene resin. The diaphragms of pumps 13, 13A and 13B and valve 85 are preferably formed from silicone rubber. The diaphragm pump housings may be formed from silicone rubber. The piston and bellows pump housings are rigid and may be formed from stainless steel, titanium, tantalum, etc. with all exposed parts coated with Silastic, Teflon, or similar material compatible with body fluids and well known for the coating of devices to be implanted within the body. The housings of the diaphragm pumps may optionally be formed from these same materials.

Dimensions are not critical and the peritoneovenous shunt system is sized to meet particular needs. At the same time, the components should be as small as possible, consistent with the needs of the patient, to facilitate implantation. The dimensions of the internal magnetic armatures are not critical so long as the magnetic force of attraction exerted between the armature and the external magnet are sufficient to maintain coupling during the pumping motion when the parts are separated by several centimeters of tissue.

It is apparent that many modifications and variations of this invention as hereinbefore set forth may be made without departing from the spirit and scope thereof. The specific embodiments described are given by way of example only and the invention is limited only by the terms of the appended claims.

We claim:

1. In an implantable anti-reflux fluid displacement pertoneovenous shunt system which comprises a fluid collecting device, a anti-reflux anti-backdiffusion, pump, an anti-reflux anti-backdiffusion non-thrombogenic catheter, and flexible tubing connecting said collecting device and pump and said pump and catheter in series, the improvement which consists in providing, as the pump of said shunt system, a magnetically driven pump having at least one variable volume chamber, a movable pumping mechanism for varying the volume of said chamber, and said pump including a magnetic armature coupled to drive the pumping mechanism and adapted for operation by a magnetic drive external of the body in which the shunt system is to be implanted.

2. An implantable anti-reflux fluid displacement peritoneovenous shunt system according to claim 1 wherein said pump comprises:
(A) a housing,
(B) a longitudinal chamber within the housing,
(C) ports at opposite ends of the housing communicating with the chamber,
(D) a pair of generally parallel spaced apart transverse flexible diaphragms within the chamber between the ports,
the peripheries of said diaphragms being in sealing engagement with the walls of the chamber, and
(E) a magnetic armature in the space between said diaphragms,
the ends of said armature being linked to and centrally supported by the diaphragms.

3. An implantable anti-reflux fluid displacement peritoneovenous shunt system according to claim 2 wherein:
(A) a plenum housing is provided having a chamber in communication with the port at one end of the pump housing and with the tubing connecting the pump and collecting device,
(B) a septum passage is provided in the plenum housing,
(C) a self-sealing puncturable closure is provided in the septum passage, and
(D) a transcutaneously operable valve is provided in the tubing between the plenum and collecting device and between the pump and catheter tip.

4. An implantable anti-reflux fluid displacement peritoneovenous shunt system according to claim 2 wherein:
(A) said longitudinal chamber is constricted between the diaphragms,
(B) said magnetic armature extends through said constriction, and
(C) bearings are supported in the wall of the constriction in engagement with the armature.

5. An implantable anti-reflux fluid displacement peritoneovenous shunt system according to claim 4 wherein a lubricating fluid is contained in the space between the diaphragms.

6. An implantable anti-reflux fluid displacement peritoneovenous shunt system according to claim 1 wherein said pump comprises:
(A) a housing,
(B) a longitudinal cylindrical chamber within the housing,
(C) ports at opposite ends of the housing communicating with the chamber,
(D) a reciprocable spool piston valve within the chamber, said valve comprising:
(1) a cylindrical magnetic armature,
(2) a central passage through the armature,
(3) an annular flange at each end of the armature, the outer peripheries of said flanges being in close sliding engagement with the chamber walls, and
(4) a check valve controlling flow through the central passage.

7. An implantable anti-reflux fluid displacement peritoneovenous shunt system according to claim 6 wherein said check valve is a pivoted flap valve overlying the central channel at one end of the spool valve.

8. An implantable anti-reflux fluid displacement peritoneovenous shunt system according to claim 6 wherein:
(A) a plenum housing is provided having a chamber in communication with the port at one end of the pump housing and with the tubing connecting the pump and collecting device,
(B) a septum passage is provided in the plenum housing,
(C) a self-sealing puncturable closure is provided in the septum passage, and
(D) a transcutaneously operable valve is provided in the tubing between the plenum and collecting device and between the pump and catheter tip.

9. An implantable anti-reflux fluid displacement peritoneovenous shunt system according to claim 1 wherein said pump comprises:
(A) a housing,
(B) a cylindrical chamber within the housing,
(C) a port communicating with the chamber,
(D) a closed end bellows within the chamber in fluid-tight sealed relationship thereto,
(E) a central screw jack including a threaded rod and nut in engagement therewith within the bellows, said threaded rod engaging the closed end of the bellows, and
(F) a rotatable magnetic armature on the nut of said screw jack for rotation therewith.

10. An implantable anti-reflux fluid displacement peritoneovenous shunt system according to claim 9 wherein said bellows contains a stable volatile liquid having the property of being in equilibrium with its vapor phase at body temperature.

* * * * *